(12) United States Patent
Stevenson

(10) Patent No.: US 6,741,274 B1
(45) Date of Patent: May 25, 2004

(54) VIDEO INSPECTION METHOD FOR INSPECTING WELDS, STRUCTURAL BEAMS, AND UNDERDECKS OF MARINE VESSELS AND LIKE STRUCTURES

(75) Inventor: Michael Stevenson, New Orleans, LA (US)

(73) Assignee: Ultrasonics and Magnetics Corporation, Harvey, LA (US)

(*) Notice: Subject to any disclaimer, the term of this patent is extended or adjusted under 35 U.S.C. 154(b) by 0 days.

(21) Appl. No.: 09/578,170

(22) Filed: May 24, 2000

Related U.S. Application Data
(60) Provisional application No. 60/135,478, filed on May 24, 1999.

(51) Int. Cl.⁷ .................................................. H04N 9/47
(52) U.S. Cl. ....................................................... 348/82
(58) Field of Search ............................. 348/82, 92, 93, 348/94, 95, 96, 207.1, 208.14, 211.99; H04N 9/47

(56) References Cited

U.S. PATENT DOCUMENTS

| | | | | |
|---|---|---|---|---|
| 3,780,224 A | * | 12/1973 | Levine | 348/38 |
| 4,750,035 A | * | 6/1988 | Chang et al. | 348/127 |
| 4,824,228 A | * | 4/1989 | Wickholm et al. | 359/377 |
| 5,016,098 A | * | 5/1991 | Cooper et al. | 348/66 |
| 5,115,307 A | * | 5/1992 | Cooper et al. | 348/66 |
| 5,251,025 A | * | 10/1993 | Cooper et al. | 348/66 |
| 5,260,834 A | * | 11/1993 | Shibata et al. | 359/690 |
| 5,285,317 A | * | 2/1994 | Uzawa | 359/676 |
| 5,290,168 A | * | 3/1994 | Cooper et al. | 433/29 |
| 5,355,818 A | * | 10/1994 | Strait et al. | 114/73 |
| 5,420,632 A | * | 5/1995 | Yamagiwa | 348/240.3 |
| 5,429,502 A | * | 7/1995 | Cooper et al. | 433/29 |
| 5,479,203 A | * | 12/1995 | Kawai et al. | 348/14.1 |
| 5,508,735 A | * | 4/1996 | Mueller | 348/82 |
| 5,515,206 A | * | 5/1996 | Peng | 359/721 |
| 5,543,840 A | * | 8/1996 | Hirota | 348/345 |
| 5,567,273 A | * | 10/1996 | Offerhaus et al. | 162/199 |
| 5,572,277 A | * | 11/1996 | Uzawa et al. | 359/686 |
| 5,808,810 A | * | 9/1998 | Mihara | 359/690 |
| 5,905,595 A | * | 5/1999 | Minami | 359/618 |
| 6,301,371 B1 | * | 10/2001 | Jones et al. | 382/106 |
| 6,401,983 B1 | * | 6/2002 | McDonald et al. | 222/181.2 |

* cited by examiner

Primary Examiner—Nhon Diep
(74) Attorney, Agent, or Firm—Garvey, Smith, Nehrbass & Doody, L.L.C.; Seth M. Nehrbass; Charles C. Garvey, Jr.

(57) ABSTRACT

A method for inspecting a marine vessel underdeck utilizes a video camera such as a digital video camera with a magnifying or telephoto lens. The method produces a magnified image on a monitor for viewing by an inspector that appears to be no more than about 24 inches away. The method includes the step of filming the underdeck of a distance of about 40–70 feet. The lens provides a focal length of between about 15 an 150 feet. Thus the method is conducted at a workable focal range of between about 15 and 150 feet. The lens preferably has a focal length of between 30 and 75 feet. The method includes the step of scanning the suspect area of the underdeck of a speed of about 1 inch per second to three feet per second. The preferred method contemplates scanning of the suspect area of a rate of about 1 foot per second.

32 Claims, 1 Drawing Sheet

VIDEO INSPECTION METHOD FOR INSPECTING WELDS, STRUCTURAL BEAMS, AND UNDERDECKS OF MARINE VESSELS AND LIKE STRUCTURES

CROSS-REFERENCE TO RELATED APPLICATIONS

Priority of my U.S. Provisional Patent Application Serial No. 60/135,478, filed May 24, 1999, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the inspection of marine vessels such as barges, bulk carriers, and tankers and particularly the underdeck structure including the beams, girders, welds, and stiffeners. Even more particularly, the present invention relates to an improved method of video inspection for barges, ships, and other marine vessels, that employs a digital video camera and a high resolution telephoto-magnifying lens that scans an area (such as a suspect area) of a vessel, such as for example the underdeck area of a barge.

2. General Background of the Invention

The inspection of marine vessels such as barges and ships requires that an inspector be within about 24 inches of the area to be inspected so that any cracks flaws, corrosion or pitting can be observed in welds, beams, girders, stringers and other structural members. This presents a problem for inspection of under deck areas of very large vessels because the underdeck area can be a long distance away from any floor or like supporting surface that could be occupied by an inspector.

To provide for inspection of under deck areas of barges, bulk carriers, and tankers, the owner is typically required "stage out" the cargo hold so that the surveyor or inspector can be placed very close to the structure being inspected. This can be a very expensive proposition costing hundreds of thousands of dollars for a very large vessel such as a four hundred foot barge.

Patents have issued that discuss video inspection using digital video cameras and a telephoto lens. The Offerhause et al. patent, U.S. Pat. No. 5,567,273, entitled "Method of Reducing Surface Irregularities in Paper Machine Head Box Components" discussed video inspection of hole inlet radii to provide further evidence of non-uniformities related to streak locations. A digital video camera inspection technique is discussed using CCD (Charged Coupled Device) technology to obtain distortion free images of superior quality and resolution. Halogen "broom" lighting is provided in order to give clear contrast and a telephoto lens to ensure a flat image. The images are then digitized for detailed computer analysis to an accuracy of 1 millimeters (0.004 inch), in a manner similar to using an optical comparator. This technique was said to be useful for inspection of the apron floor joint, turbulence generator perforated plate, and inlet tube bank.

The Mueller patent, U.S. Pat. No. 5,508,735, entitled "Underdeck Inspection Device" relates to an apparatus and method for the remote visualization and inspection of an internal storage space, such as a ship's hold. The apparatus includes a mounting stand to which is rotationally mounted a support shaft, the support shaft having a camera and a light source secured thereto. The camera and light source rotate with the support shaft, and are pivotally movable relative to the support shaft. A drive shaft extends through the support shaft and is operable to simultaneously pivot the light source camera. A light adjustment drive shaft is mounted to the hollow support shaft and allows the operator to pivot the light source independently of the camera to permit a wider field of view than would otherwise be available. The apparatus is inserted, via an access opening, into a storage space and thereafter operated to allow an inspector, located outside of the storage space, to visually inspect the surfaces surrounding and defining the storage space. The Mueller device does not cover corner areas because it rotates about a fixed center.

A stereo microscopic inspection system that employs a telephoto objective assembly is the subject of U.S. Pat. No. 4,824,228.

Electronic video dental cameras that employ telephoto lenses are disclosed in U.S. Pat. Nos. 5,016,098; 5,115,307; 5,251,025; and 5,429,502. Other patents that discuss the use of a telephoto lens with a video camera include U.S. Pat. Nos. 5,808,810; 5,572,277; 5,543,840; 5,515,206; 5,479,203; 5,420,632; 5,290,168; 5,285,317; and 5,260,834.

BRIEF SUMMARY OF THE INVENTION

The present invention provides an improved method for video inspection of the inside of a marine vessel, barge, ship, etc. The present invention provides an apparatus and a method for inspecting surfaces including those that are suspect such as welds, beams, underdeck surface, girders and the like. The present invention provides full coverage even into corners, and the coverage is overlapping.

For the method of the present invention, there is provided a video camera having a lens. The lens is preferably a telephoto lens and/or magnifying lens that provides a close-up view for an inspector that views a monitor or a video tape after inspection is completed. Preferably, the inspector views the monitor in real time while the inspection is occurring.

As part of the method, the underdeck for example of a barge is filmed from a distance of far away such as 15–75 feet and preferably from a distance of 40–70 feet.

The lens has a focal length of between 5 feet and infinity, preferably a focal length of between 15 and 150 feet.

When the video image appears on a monitor, it is magnified and preferably appears less than 24 inches away from the inspector.

This method provides a high resolution close-up image that enables an inspector to view the video tape image and spot any cracks, pitting, corrosion, flaws, etc.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
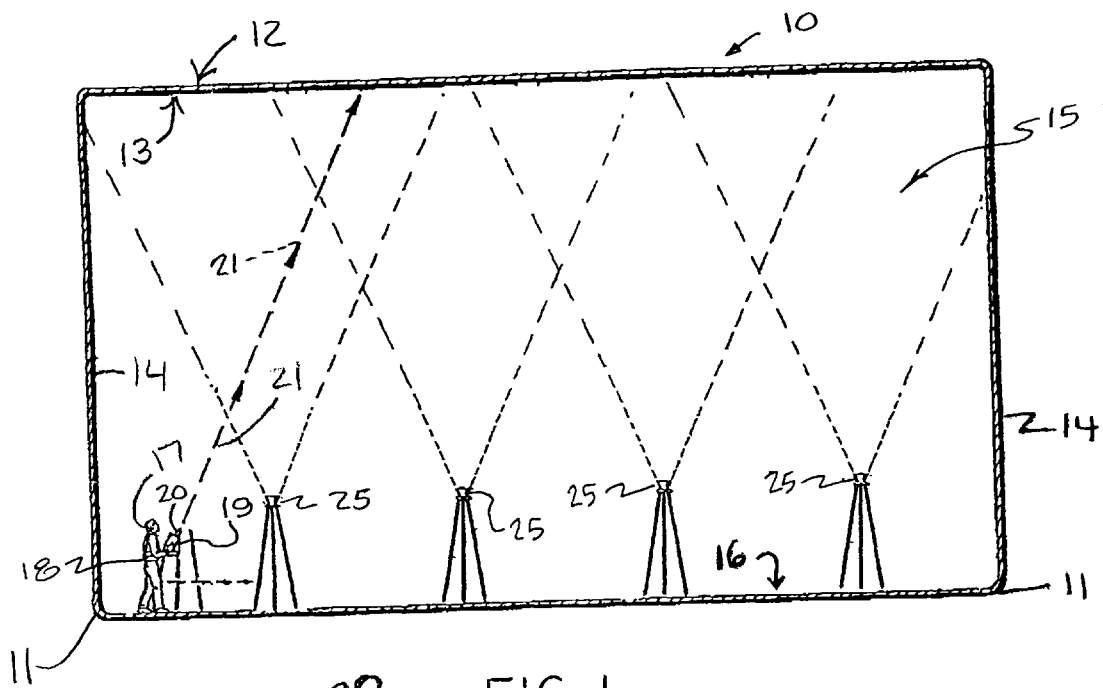
FIG. 1 is a schematic side elevational view showing the method and apparatus of the present invention.
Figure 2:
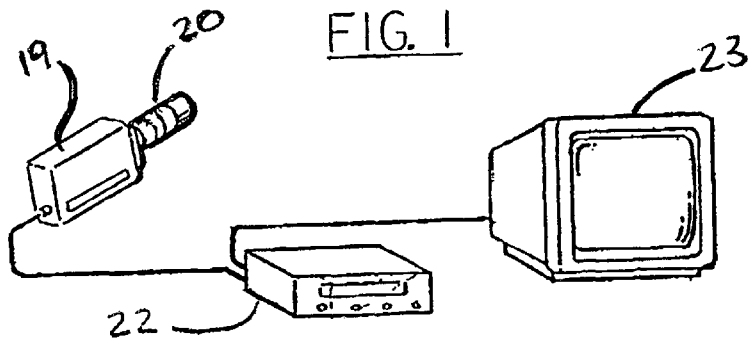
FIG. 2 is a schematic diagram showing the apparatus of the present invention.
Figure 3:
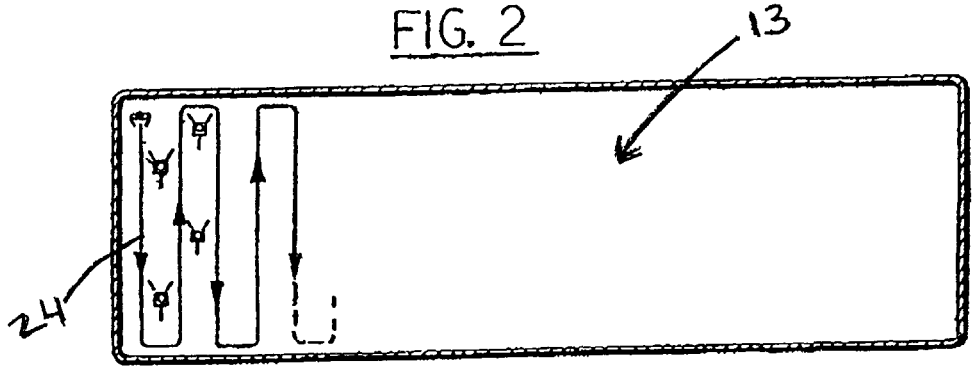
FIG. 3 is a plan view illustrating the method of the present invention.

FIGS. 1 shows the apparatus of the present invention designated generally by the numeral 10. In FIGS. 1–3, inspection apparatus 10 is shown in use to film the underdeck area of a marine vessel 11. Vessel 11 such as a barge has an interior hold 15 surrounded by deck, floor, and side walls. In FIG. 1, vessel 11 has a hold 15 that is surrounded by deck 12, walls 14 and floor 16. An underdeck 13 is typically the area to be inspected for pitting, cracks, and other flaws. Underdeck 13 can include plate, structural members, welds, beams, and girders, for example.

The method of the present invention contemplates the inspection of structural members, welds, beams, girders and plates. In FIG. 1, an inspector 17 wears a harness 18 that supports digital camera 19. The harness if preferably a steadying type harness such as the commercially available Glidecam® 1000 Pro harness. In FIG. 2, a schematic diagram shows digital video camera 19 with a telephoto/magnifying lens 20. During inspection of the barge underdeck 13, monitor 23 can be viewed in real time, or a recorder 22 can be used to record a video tape of the underdeck 13 for later coup visualization. Preferably powerful fighting units 26 illuminate the underdeck 13 to remove any shadows. At the time of the inspection, monitor 23 can be connected to the camera 19 with recorder 22 for simultaneously recording and inspecting for cracks, pitting, flaws, etc. In such a case, both real time and subsequent inspection is enabled. The film recorded by recorder 22 can preferably be later viewed and/or analyzed.

In FIG. 3, the barge underdeck 13 is shown schematically, wherein an inspection path 24 is mapped out as a preselected grid. For example, the image captured by the camera 19 and lens 20 can be for example between about 6 inches and 2 feet in diameter. The inspection path 24 would preferably be an overlapping grid path so that the video images overlap six inches, for example.

The method of the present invention thus provides a quick, simple yet workable solution to the problem of inspecting the underdeck of a barge or other remote surface to be inspected. With the present invention, there is no need for complicated scaffolding, robotic arm, or like equipment. The inspector 17 simply needs to obtain access to the hold 15 so that the areas can be filmed from a distance, preferably between 15 and 150 feet.

The present invention utilizes components that are commercially available such as a digital camera available from Canadian Photonic Labs. The lenses can be telephoto lenses such as a 500 millimeter fixed aperture mirror lens manufactured by Samyang. The lenses can be modified to provide a focal length of between about 15 and 150 feet, preferably between about 30 and 75 feet.

The present invention can be used to inspect welds, beams, plate, coating, etc. for pitting corrosion or flaws in underdeck areas of ships or other marine vessels.

The following table lists the parts numbers and parts descriptions as used herein and in the drawings attached hereto.

PARTS LIST

| Part Number | Description |
| --- | --- |
| 10 | inspection apparatus |
| 11 | marine vessel |
| 12 | deck |
| 13 | underdeck |
| 14 | wall |
| 15 | hold |
| 16 | floor |
| 17 | inspector |
| 18 | harness |

-continued

PARTS LIST

| Part Number | Description |
| --- | --- |
| 19 | digital video camera (preferably one that takes motion pictures) |
| 20 | telephoto lens |
| 21 | line of sight |
| 22 | recorder |
| 23 | monitor |
| 24 | inspection path |
| 25 | lighting unit |

The video camera can be either digital (preferably) or analog. For example (and preferably), the video camera could record digitally on a video tape.

As used herein, the term "film" can mean a motion picture recorded on a video tape.

Though this invention has been described in conjunction with barges, the present invention can advantageously be used with other vessels.

The foregoing embodiments are presented by way of example only; the scope of the present invention is to be limited only by the following claims.

What is claimed is:

1. A method of inspecting a vessel underdeck comprising the steps of:
    a) providing a video camera with a telephoto lens;
    b) filming the underdeck from a distance of between 40 and 70 feet to generate a visual record on a video tape or monitor;
    c) wherein the lens has a focal length of between 5 and 150 feet; and
    d) reviewing the visual record to inspect for defects.

2. A method of inspecting a vessel underdeck comprising the steps of:
    a) providing a video camera with a telephoto lens;
    b) filming the underdeck following a selected grid path from a distance of between 40 and 70 feet to generate a visual record on a video tape or monitor;
    c) wherein the lens has a focal length of 15 to 75 feet; and
    d) reviewing the visual record to inspect for defects.

3. A method of inspecting a vessel underdeck comprising the steps of:
    a) providing a video camera with a telephoto lens;
    b) filming the underdeck while following a selected grid path from a distance of between 40 and 70 feet to generate a visual record on a video tape or monitor; and
    c) wherein the lens has a focal length of 30 to 75 feet; and
    d) reviewing the visual record to inspect for defects.

4. A method of inspecting a vessel underdeck comprising the steps of:
    a) providing a video camera with a telephoto lens;
    b) filming the underdeck while following a selected grid path that includes a plurality of overlapping paths from a distance of between 40 and 70 feet; and
    c) wherein the video image appears on a monitor to be magnified and less than 24 inches away.

5. A method of inspecting a vessel underdeck comprising the steps of:
    a) providing a video camera with a telephoto lens;
    b) using the video camera to view the underdeck from a distance of between 40 and 70 feet; and c) wherein the lens has a focal length of between 5 and 150 feet.

6. A method of inspecting a vessel underdeck comprising the steps of:
   a) providing a video camera with a telephoto lens;
   b) using the video camera to view the underdeck from a distance of between 40 and 70 feet; and
   c) wherein the lens has a focal length of 15 to 75 feet.

7. A method of inspecting a vessel underdeck comprising the steps of:
   a) providing a video camera with a telephoto lens;
   b) using the video camera to view the underdeck from a distance of between 40 and 70 feet; and
   c) wherein the lens has a focal length of 30 to 75 feet.

8. A method of inspecting a vessel underdeck comprising the steps of:
   a) providing a video camera with a telephoto lens;
   b) using the video camera to view the underdeck from a distance of between 40 and 70 feet; and
   c) wherein the video image appears on a monitor to be magnified and less than 24 inches away.

9. The method of claim 1, further comprising the step of scanning the underdeck.

10. The method of claim 1, further comprising the step of scanning the underdeck at a speed of about 1 inch per second to about three feet per second.

11. The method of claim 1, further comprising the step of scanning the underdeck at a speed of about 1 foot per second.

12. The method of claim 1, further comprising filming the underdeck while following a selected grid path that includes a plurality of overlapping paths.

13. The method of claim 1, further comprising inspecting the underdeck while following a selected grid path that includes a plurality of overlapping paths.

14. A method of inspecting a vessel hold that has multiple surfaces including a floor surface, an under deck surface, and side wall surfaces, comprising the steps of:
   a) providing a video camera with a telephoto lens;
   b) positioning the video camera in between the floor and ceiling, but closer to the floor;
   c) generating a video record that can be viewed by an inspector;
   d) wherein the lens has a focal length of between 5 and 150 feet; and
   e) reviewing the visual record to inspect for defects.

15. The method of claim 14, further comprising the step of scanning the under deck surface.

16. The method of claim 14, further comprising the step of scanning the under deck surface at a speed of about 1 inch per second to about three feet per second.

17. The method of claim 14, further comprising the step of scanning the under deck surface at a speed of about 1 foot per second.

18. The method of claim 14, further comprising filming the under deck surface while following a selected grid path that includes a plurality of overlapping paths.

19. The method of claim 14, further comprising inspecting the under deck surface while following a selected grid path that includes a plurality of overlapping paths.

20. A method of inspecting a vessel hold that includes a floor, side walls and a hold ceiling, comprising the steps of:
   a) providing a video camera with a telephoto lens;
   b) filming the ceiling while following a selected grid path;
   c) positioning the video camera in between the floor and ceiling, but closer to the floor;
   d) wherein an inspector moves the camera to follow the selected grid path in step "b"; and
   e) reviewing the visual record to inspect for defects.

21. The method of claim 20 wherein in step "d" a videotape record is generated.

22. The method of claim 20 wherein in step "d" a visual record is displayed on a monitor.

23. The method of claim 20, further comprising the step of scanning the under deck surface.

24. The method of claim 14, further comprising the step of scanning the under deck surface at a speed of about 1 inch per second to about three feet per second.

25. The method of claim 14, further comprising the step of scanning the under deck surface at a speed of about 1 foot per second.

26. The method of claim 14, further comprising filming the under deck surface while following a selected grid path that includes a plurality of overlapping paths.

27. A method of inspecting a vessel hold having a floor, side walls and a ceiling, comprising the steps of:
   a) providing a video camera with a telephoto lens;
   b) positioning the video camera in between the floor and ceiling, but closer to the floor;
   c) filming the ceiling while following a selected grid path to generate a visual record; and
   d) wherein the lens has a focal length of between about 30 to 75 feet; and
   e) reviewing the visual record to inspect for defects.

28. The method of claim 27, further comprising the step of scanning the under deck.

29. The method of claim 27, further comprising the step of scanning the under deck at a speed of about 1 inch per second to about three feet per second.

30. The method of claim 27, further comprising the step of scanning the under deck at a speed of about 1 foot per second.

31. The method of claim 27, further comprising filming the under deck while following a selected grid path that includes a plurality of overlapping paths.

32. The method of claim 27, further comprising inspecting the under deck while following a selected grid path that includes a plurality of overlapping paths.

* * * * *